United States Patent
Hyun et al.

(10) Patent No.: US 8,043,489 B2
(45) Date of Patent: Oct. 25, 2011

(54) MULTI-LAYER STRIP FOR USE IN MEASURING BIOLOGICAL MATERIAL AND SYSTEM FOR MEASURING BIOLOGICAL MATERIAL

(75) Inventors: Seok Jung Hyun, Seoul (KR); Kyung Hoo Moon, Seoul (KR); Kyu Sik Yun, Seoul (KR); Yeon Jae Kang, Seoul (KR); Guei Sam Lim, Seoul (KR); Gyoung Soo Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 859 days.

(21) Appl. No.: 12/017,968

(22) Filed: Jan. 22, 2008

(65) Prior Publication Data
US 2008/0202928 A1    Aug. 28, 2008

(30) Foreign Application Priority Data
Jan. 23, 2007  (KR) .................. 10-2007-0006996

(51) Int. Cl.
*G01N 27/327* (2006.01)
*G01N 33/52* (2006.01)
(52) U.S. Cl. .................. 204/403.03; 422/82.05
(58) Field of Classification Search .............. 204/403.01–403.15, 641; 435/173.4–173.6, 287.1–288.7, 4; 422/68.1–98; 436/149–150, 164, 165, 169, 170
See application file for complete search history.

(56) References Cited

U.S. PATENT DOCUMENTS

| | | | |
|---|---|---|---|
| 2002/0110486 A1* | 8/2002 | Shartle et al. | 422/57 |
| 2003/0212344 A1* | 11/2003 | Yuzhakov et al. | 600/583 |
| 2004/0191124 A1 | 9/2004 | Noetzel et al. | |
| 2005/0130236 A1* | 6/2005 | Goldman | 435/7.21 |
| 2007/0275193 A1* | 11/2007 | DeSimone et al. | 428/34.1 |

FOREIGN PATENT DOCUMENTS
JP   2005-106559 A   4/2005
WO  WO-2006/130299 A2   12/2006
* cited by examiner

*Primary Examiner* — Kaj K Olsen
*Assistant Examiner* — Susan Thai
(74) *Attorney, Agent, or Firm* — Birch, Stewart, Kolasch & Birch, LLP

(57) ABSTRACT

The multi-layer strip for use in measuring biological material and the system for measuring a biological material are provided, wherein the multi-layer strip includes a stack of a plurality of strips, each having a flow channel and a reaction unit, and the strips may react with specific materials contained in a biological material injected into the multi-layer strip. Thus, it is possible to quantitatively analyze various materials contained in a biological material and to optically and electrochemically measure and quantitatively analyze various materials in a biological material.

20 Claims, 8 Drawing Sheets

MULTI-LAYER STRIP FOR USE IN MEASURING BIOLOGICAL MATERIAL AND SYSTEM FOR MEASURING BIOLOGICAL MATERIAL

CROSS-REFERENCE TO RELATED APPLICATION

This application claims priority from Korean Patent Application No. 10-2007-0006996 filed on Jan. 23, 2007 in the Korean Intellectual Property Office, the disclosure of which is incorporated herein by reference in its entirety.

BACKGROUND OF THE INVENTION

1. Field of the Invention

The present invention relates to a multi-layer for use in measuring biological material and a system for measuring biological material.

2. Description of the Related Art

Devices capable of measuring and analyzing biological materials have recently been developed and widely used in the medical field.

Such biological material measurement devices determine whether body fluid such as blood, urine or saliva contains specific materials and thus determine whether individuals are healthy.

For example, in order to control and monitor diabetes, the amount of glucose in blood may need to be periodically measured.

In order to measure glucose, portable glucose measurement devices or strip-type bio sensors may be used.

Various types of devices such as portable measurement devices or stripe-type bio sensors may be used to measure and analyze biological materials. However, conventional biological material measurement devices alone cannot selectively analyze specific materials (e.g., glucose) contained in a biological material sample. Therefore, conventional biological material measurement devices have limited effectiveness and limited range of application.

SUMMARY OF THE INVENTION

Aspects of the present invention provide a multi-layer strip for use in measuring biological material and a system for measuring a biological material. The multi-layer strip includes a stack of a plurality of strips, each having a flow channel and a reaction unit, and can thus react with various materials contained in a biological material injected thereinto. The system measures the degree of reaction of the various materials in the given biological material with the strips and quantitatively analyzes the various materials.

Aspects of the present invention also provide a multi-layer strip for use in measuring biological material and a system for measuring a biological material which can optically and electrochemically measure and quantitatively analyze various materials contained in a given biological material.

According to an aspect of the present invention, there is provided a multi-layer strip for use in measuring a biological material, the multi-layers trip including: a stack of a plurality of strips, each strip having a flow channel through which a biological material is injected into the multi-layer strip and a reaction unit which reacts with the biological material; and a plurality of reaction-inducing material layers which are respectively immobilized in the reaction units of the strips and react with the biological material.

According to another aspect of the present invention, there is provided a multi-layer strip for measuring a biological material, the multi-layers trip including: a stack of a plurality of strips having an electrochemical strip for electrochemically measuring the reaction of a biological material, each strip having a flow channel through which the biological material is injected into the multi-layer strip and a reaction unit which reacts with the biological material; and a plurality of reaction-inducing material layers which are respectively immobilized in the reaction units of the strips and react with specific materials contained in the biological material.

According to another aspect of the present invention, there is provided a system for measuring a biological material, the system including: a multi-layer strip which includes a stack of a plurality of strips and a plurality of reaction-inducing material layers, each of the strips having a flow channel through which a biological material is injected into the multi-layer strip and a reaction unit which reacts with the biological material, and the reaction-inducing material layers being immobilized in the reaction units of the strips and reacting with the biological material; and an optical processing module which optically measures the degree of reaction of the biological material with the reaction-inducing material layers and quantitatively analyzes the results of the optical measurement.

BRIEF DESCRIPTION OF THE DRAWINGS

The above and other features and advantages of the present invention will become more apparent by describing in detail preferred embodiments thereof with reference to the attached drawings, in which.

DETAILED DESCRIPTION OF THE INVENTION

The present invention will now be described more fully with reference to the accompanying drawings, in which exemplary embodiments of the invention are shown.

Figure 1:
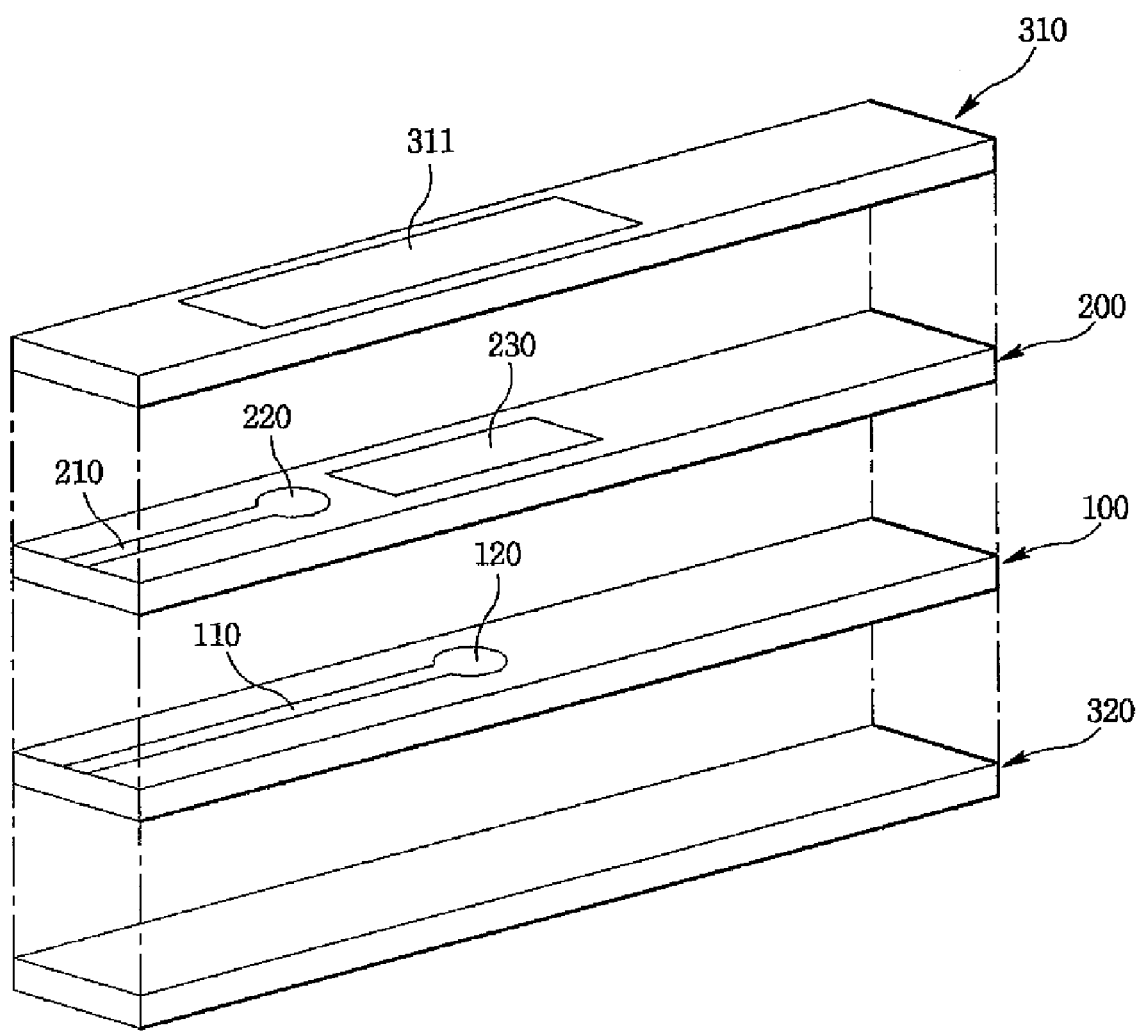
FIG. 1 illustrates an exploded perspective view of a multi-layer strip for use in measuring a biological material according to an embodiment of the present invention.

FIG. 1 illustrates an exploded perspective view of a multi-layer strip for use in measuring a biological material according to an embodiment of the present invention. Referring to FIG. 1, the multi-layer strip includes a stack of first and second strips 100 and 200. The first strip 100 includes a first flow channel 110 through which a biological material is injected into the first strip 100; and a first reaction unit 120 which reacts with the biological material. Likewise, the second strip 200 includes a second flow channel 210 through which the biological material is injected into the second strip 200; and a second reaction unit 220 which reacts with the biological material.

Reaction-inducing materials (not shown) that react with specific materials contained in the predetermined biological material may be respectively immobilized in the first and second reaction units 120 and 220.

Preferably, the reaction-inducing materials immobilized at the reaction units(120,220) of the first and second strip(100, 200) are the ones that react with other specific materials contained in the biological materials.

In short, the reaction-inducing material layers react with each different specific materials contained in the biological material.

For example, a reaction-inducing material that reacts with cholesterol may be immobilized in the first reaction unit 120 of the first strip 100, and a reaction-inducing material that reacts with hemoglobin may be immobilized in the second reaction unit 220 of the second strip 200.

The predetermined biological material may be a body fluid such as blood, urine, serum, saliva, or urine.

The first and second flow channels 110 and 210 may be nano-channels each having a width of several nanometers to several hundreds of nanometers and may thus enable a liquid-phase biological material to be injected into the first and second reaction units 120 and 220 by means of a capillary phenomenon.

The first flow channel 110 may be connected to the first reaction unit 120, and the second flow channel 210 may be connected to the second reaction unit 220.

The multi-layer strip is illustrated in FIG. 1 as including a stack of two strips, but the present invention is not restricted to this. That is, the multi-layer strip may be a stack of more than two strips.

Since a biological material is injected into and reacts with each of the multi-layer strip, it is possible to quantitatively analyze a plurality of specific materials contained in the biological material by optically or electrochemically analyzing the degree to which the specific materials reacts with the multi-layer strip. For example, when blood is injected into the multi-layer strip, it is possible to quantitatively analyze a number of components of blood such as glucose, cholesterol, and hemoglobin.

In short, the multi-layer strip of the embodiment of FIG. 1 includes a stack of a plurality of strips, each having a flow channel and a reaction unit; and a plurality of reaction-inducing material layers which are immobilized in the respective strips and can react with specific materials contained in a biological material.

The multi-layer strip of the embodiment of FIG. 1 optically measures the degree of reaction of a biological material injected thereinto with the first and second reaction units 120 and 220 of the first and second strips 100 and 200. The first and second reaction units 120 and 220 of the first and second strips 100 and 200 do not overlap each other so that light perpendicularly incident thereupon can smoothly transmit through each of the strips. Each of the first and second strips 100 and 200 may include a transparent region which can transmit light therethrough so that the light can reach the reaction unit of a corresponding underlying strip, if any.

Referring to FIG. 1, the second strip 200 includes a transparent region 230 which is disposed close to the second reaction unit 220. The first reaction unit 120 of the first strip 100 is disposed below the transparent region 230 of the second strip 200.

Referring to FIG. 1, the multi-layer strip also includes upper and lower cover strips 310 and 320 which are attached onto the top and the bottom, respectively, of a stack of the first and second strips 100 and 200.

At least one of the upper and lower cover strips 310 and 320 may include a transparent region 311 which can transmit light therethrough so that the light can reach the first and second reaction units 120 and 220 of the first and second strips 100 and 200.

FIG. 1 does not illustrated any transparent region formed at the lower cover strip 320.

Figure 2A:
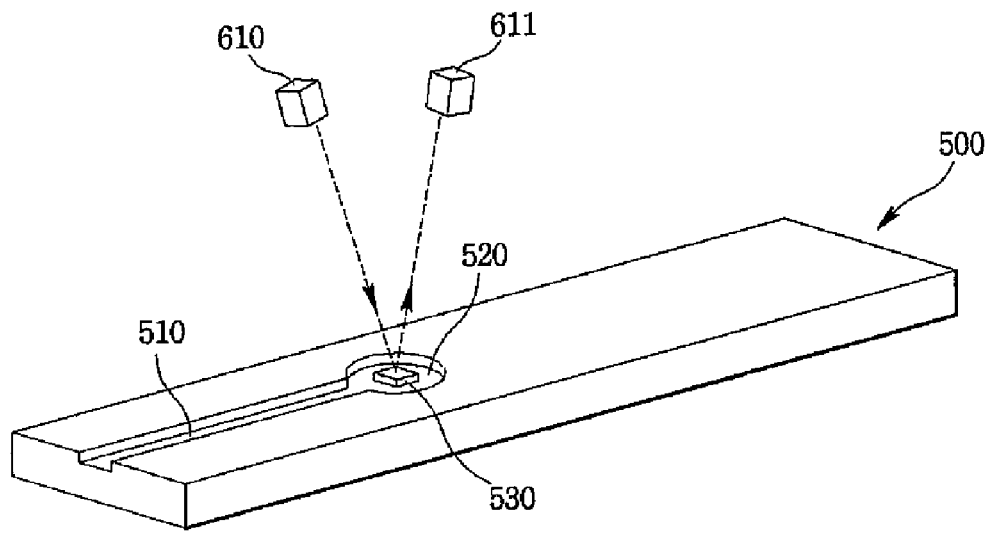
FIGS. 2A and 2B illustrate diagrams for explaining a method of optically analyzing biomaterials using the multi-layer strip illustrated in FIG. 1, according to an embodiment of the present invention.
Figure 2B:
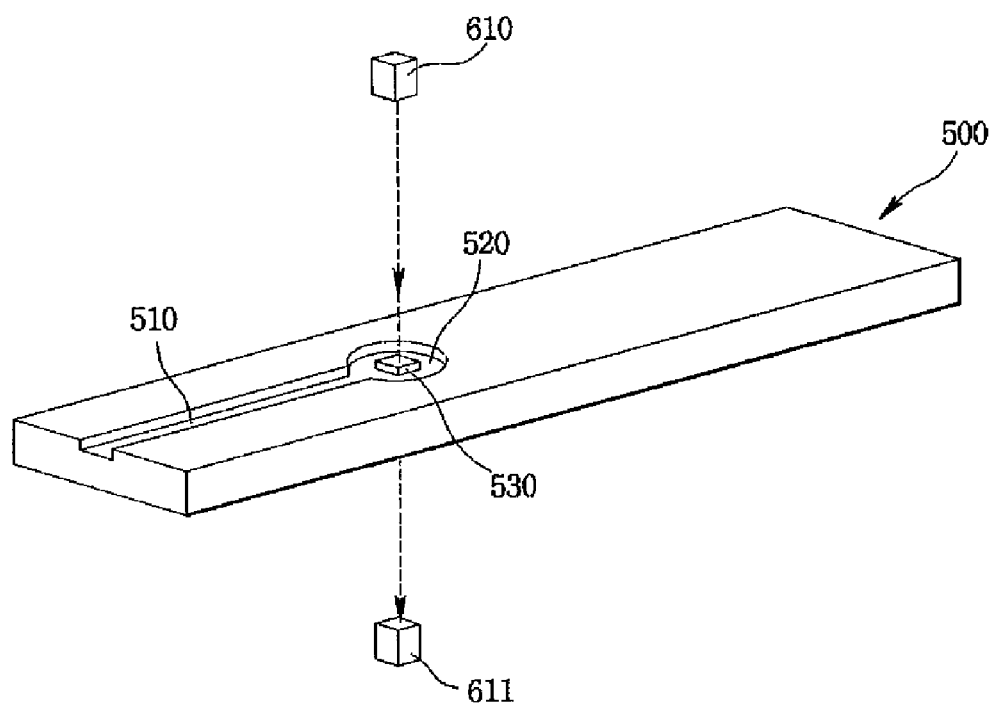

FIGS. 2A and 2B illustrate diagrams for explaining a method of optically analyzing a biological material using the multi-layer strip illustrated in FIG. 1. Referring to FIGS. 2A and 2B, when a biological material is injected into a reaction unit 520 of a strip 500 through a flow channel 510, a specific material contained in the biological material reacts with a reaction-inducing material layer 530 immobilized in the reaction unit 520.

Then, referring to FIG. 2A, a light emitter 610 irradiates light onto an area in which the reaction of the specific material in the biological material with the reaction-inducing material layer 530 takes place, and a light receiver 611 detects light reflected from the strip 500.

Alternatively, referring to FIG. 2B, the light emitter 610 irradiates light onto the area where the reaction of the specific material in the biological material with the reaction-inducing material layer 530 takes place, and the light receiver 611 detects light transmitted through the strip 500.

Thereafter, the specific material in the biological material may be quantitatively analyzed based on the amount of light detected by the light receiver 611.

A color variation at a region where the specific material contained in the biological material and the reaction-inducing material layer 530 is measured, and the specific material can be quantitatively analyzed by a intensity of light reflected from or transmitted through the reaction-inducing material layer 530.

Figure 3:
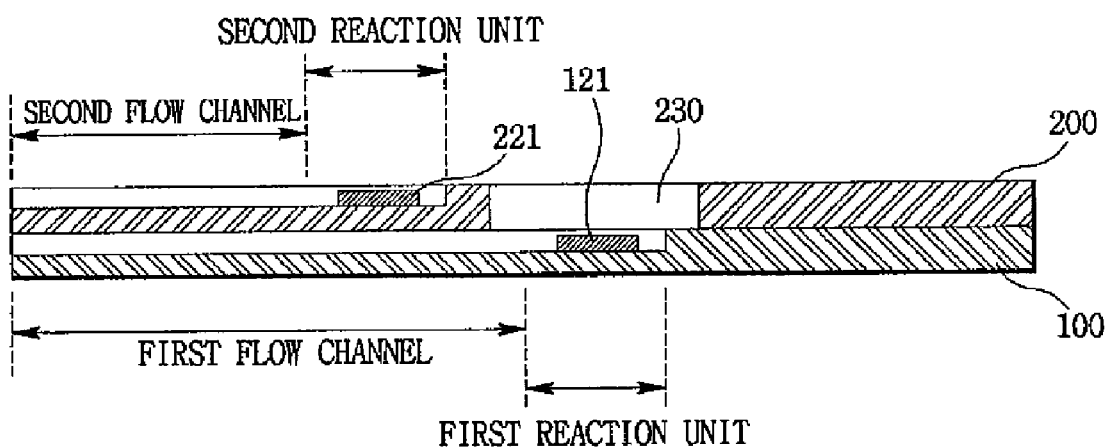
FIG. 3 illustrates a cross-sectional view of a multi-layer strip for use in measuring a biological material according to an embodiment of the present invention.

FIG. 3 illustrates a cross-sectional view of a multi-layer strip for use in measuring a biological material according to an embodiment of the present invention.

Referring to FIG. 3, a second strip 200 is deposited on a first strip 100. The first strip 100 includes a first flow channel through which a biological material can be injected into the multi-layer strip and a first reaction unit which can react with the biological material. Likewise, the second strip 200 includes a second flow channel through which a biological material can be injected into the multi-layer strip and a second reaction unit which can react with the biological material.

The first and second reaction units of the first and second strips 100 and 200 do not overlap each other.

The second strip 200 includes a transparent region 230 which can transmit light therethrough so that the light can reach the first reaction unit of the first strip 100.

Reaction-inducing material layers 121 and 221 are respectively formed in the first and second reaction units of the first and second strips 100 and 200.

The first and second flow channels and the first and second reaction units of the first and second strips 100 and 200 may be formed as grooves or through holes, as illustrated in FIG.

3, so that a biological material can be smoothly injected into the stack of the first and second strips 100 and 200.

Figure 4:
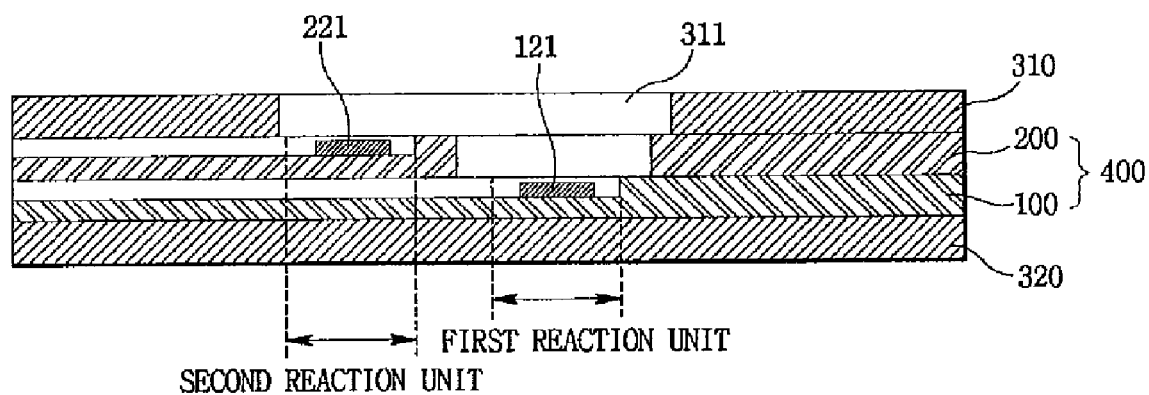
FIG. 4 illustrates a cross-sectional view of an embodiment of the multi-layer strip illustrated in FIG. 1.

FIG. 4 illustrates a cross-sectional view of an embodiment of the multi-layer strip illustrated in FIG. 1. Referring to FIG. 4, upper and lower cover strips 310 and 320 are attached onto the top and the bottom, respectively, of a stack 400 of first and second strips 100 and 200.

In order to irradiate light onto the first and second reaction units of the first and second strips 100 and 200, a transparent region 311 may be formed over a wide area of the upper cover strip 310.

A transparent region (not shown) may also be formed in the second strip 200 so that light incident upon the second strip 200 can transmit through the second strip 200 and can be incident upon the first reaction unit of first strip 100.

In the embodiment of FIG. 4, like in the embodiment of FIG. 2A, a light emitter, which is disposed above the upper cover strip 310, irradiates light onto the multi-layer strip, and a light receiver, which is also disposed above the upper cover strip 310, detects light reflected from a reaction point in the multi-layer strip.

The reaction point may be a place where a biological material injected into the multi-layer strip reacts with a reaction-inducing material in the multi-layer strip. Referring to FIG. 4, first and second reaction-inducing material layers 121 and 221 are respectively formed in the first and second reaction units of the first and second strips 100 and 200.

Figure 5:
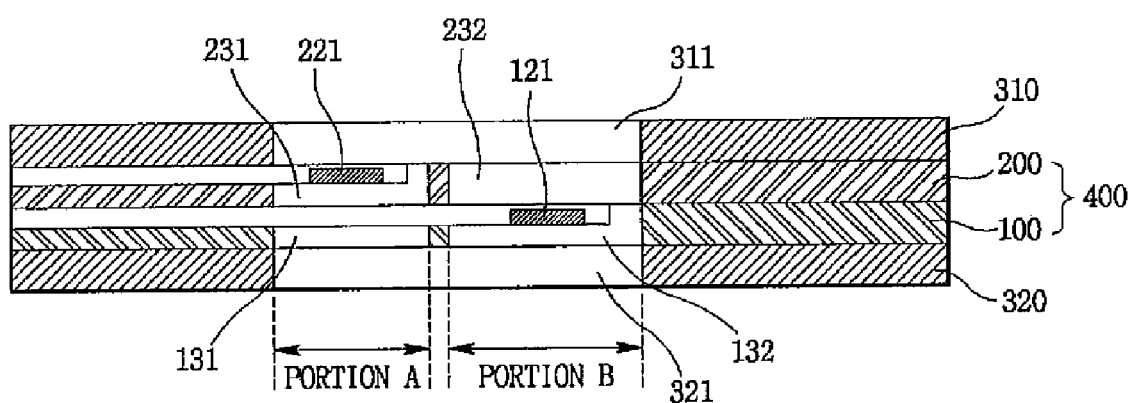
FIG. 5 illustrates a cross-sectional view of another embodiment of the multi-layer strip illustrated in FIG. 1.

FIG. 5 illustrates a cross-sectional view of another embodiment of the multi-layer strip illustrated in FIG. 1. Referring to FIG. 5, a transparent region 311 is formed in an upper cover strip 310, which is stacked onto a stack 400 of the first and second strips 100 and 200. The transparent region 311 may be used to irradiate light onto the first and second reaction units of the first and second strips 100 and 200.

A transparent region 321 is formed in a lower cover strip 320, which is attached onto the bottom of the stack 400. The transparent region 321 transmits therethrough light transmitted through the first and second reaction units of the first and second strips 100 and 200.

Transparent regions 131 and 132 are formed in the first strip 100, and transparent regions 231 and 232 are formed in the second strip 200. The transparent regions 311, 321, 131, 132, 231 and 232 are connected to one another, and thus, light incident upon the multi-layer strip can smoothly transmit through the multi-layer strip.

That is, in order to enable light irradiated onto the first reaction unit of the first strip 100 through the transparent region 311 of the upper cover strip 310 to reach the transparent region 321 of the lower cover strip 320 through a reaction point in the multi-layer strip, portion A of the multi-layer strip may be formed to be transparent, as illustrated in FIG. 5.

In addition, in order to enable light irradiated onto the second reaction unit of the second strip 200 through the transparent region 311 of the upper cover strip 310 to reach the transparent region 321 of the lower cover strip 320 through the reaction point in the multi-layer strip, portion B of the multi-layer strip may be formed to be transparent, as illustrated in FIG. 5.

In the embodiment of FIG. 5, like in the embodiment of FIG. 2B, a light emitter, which is disposed above the upper cover strip 310, irradiates light onto the multi-layer strip, and a light receiver, which is disposed below the lower cover strip 320, detects light transmitted through a reaction point in the multi-layer strip.

Figure 6:
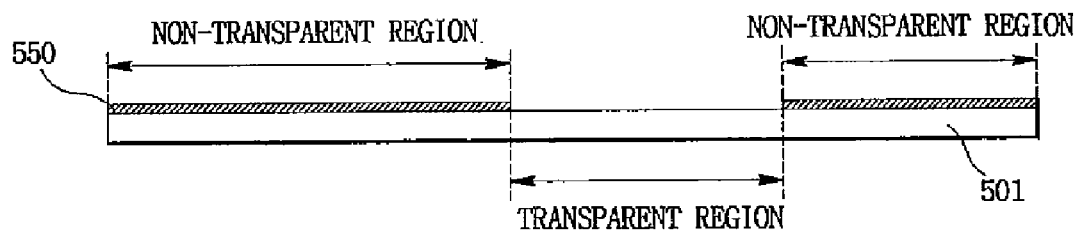
FIG. 6 illustrates a cross-sectional view for explaining a method of forming a transparent region in a strip according to an embodiment of the present invention.

FIG. 6 illustrates a cross-sectional view of a method of forming a transparent region in a strip according to an embodiment of the present invention. In order to form a transparent region in the plurality of strips, the plurality of strips are formed with transparent strips, and the transparent strips are patterned by opaque material layer.

The transparent region of the plurality of strips may be defined by the strip region not covered with the opaque material layer.

That is, referring to FIG. 6, when opaque material layer patterns 550 are formed on a transparent strip 501, the regions of the transparent strip 501 on which the opaque material layer patterns 550 are formed may be defined as non-transparent regions that cannot transmit light therethrough, and region of the transparent strip 501 on which the opaque material layer patterns 550 are not formed may be defined as a transparent region that can transmit light therethrough.

Figure 7:
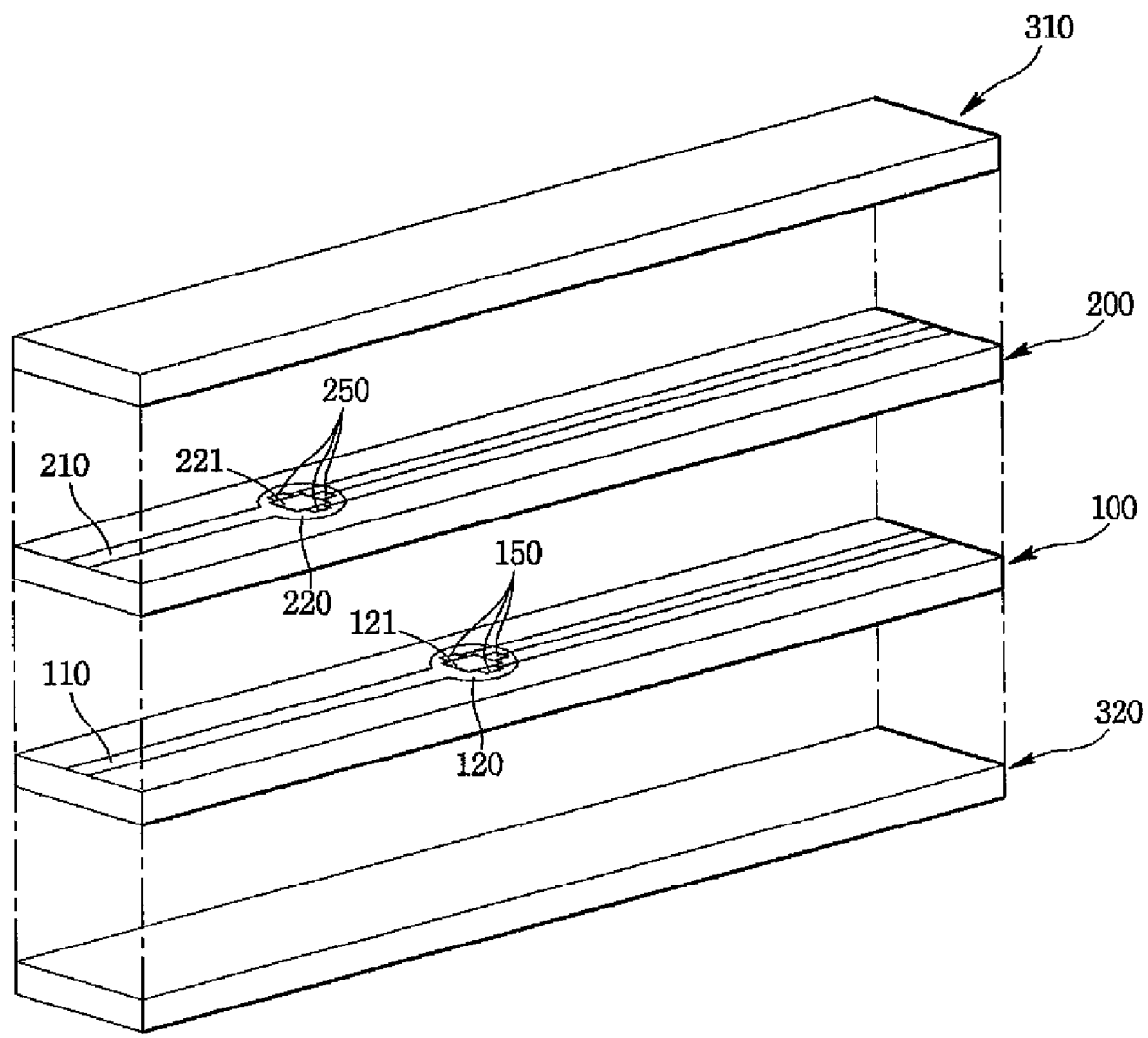
FIG. 7 illustrates an exploded perspective view of a multi-layer strip for measuring a biological material according to another embodiment of the present invention.

FIG. 7 illustrates an exploded perspective view of a multi-layer strip for measuring a biological material according to another embodiment of the present invention. Referring to FIG. 7, the multi-layer strip includes a stack of first and second strips 100 and 200. The first and second strips 100 and 200 include first and second reaction units 120 and 220, respectively. First and second reaction-inducing material layers 121 and 221 are immobilized in the first and second reaction units 120 and 220, respectively, and may react with specific materials contained in a biological material injected into the multi-layer strip.

The multi-layer strip of the embodiment of FIG. 7 electrochemically measures the degree of reaction of a biological material injected thereinto with the reaction units of the first and second strips 100 and 200. For this, first and second sensing electrode patterns 150 and 250 are formed in the first and second reaction units 120 and 220, respectively. First and second reaction-inducing material layers 121 and 221 are formed on the first and second sensing electrode patterns 150 and 250, respectively.

The first and second sensing electrode patterns 150 and 250 detect current variations resulting from the reaction of the first and second reaction-inducing material layers 121 and 221 with a biological material injected into the multi-layer strip.

The first and second sensing electrode patterns 150 and 250 may be triode patterns, each having a working electrode, a reference electrode and a counter electrode.

Figure 8:
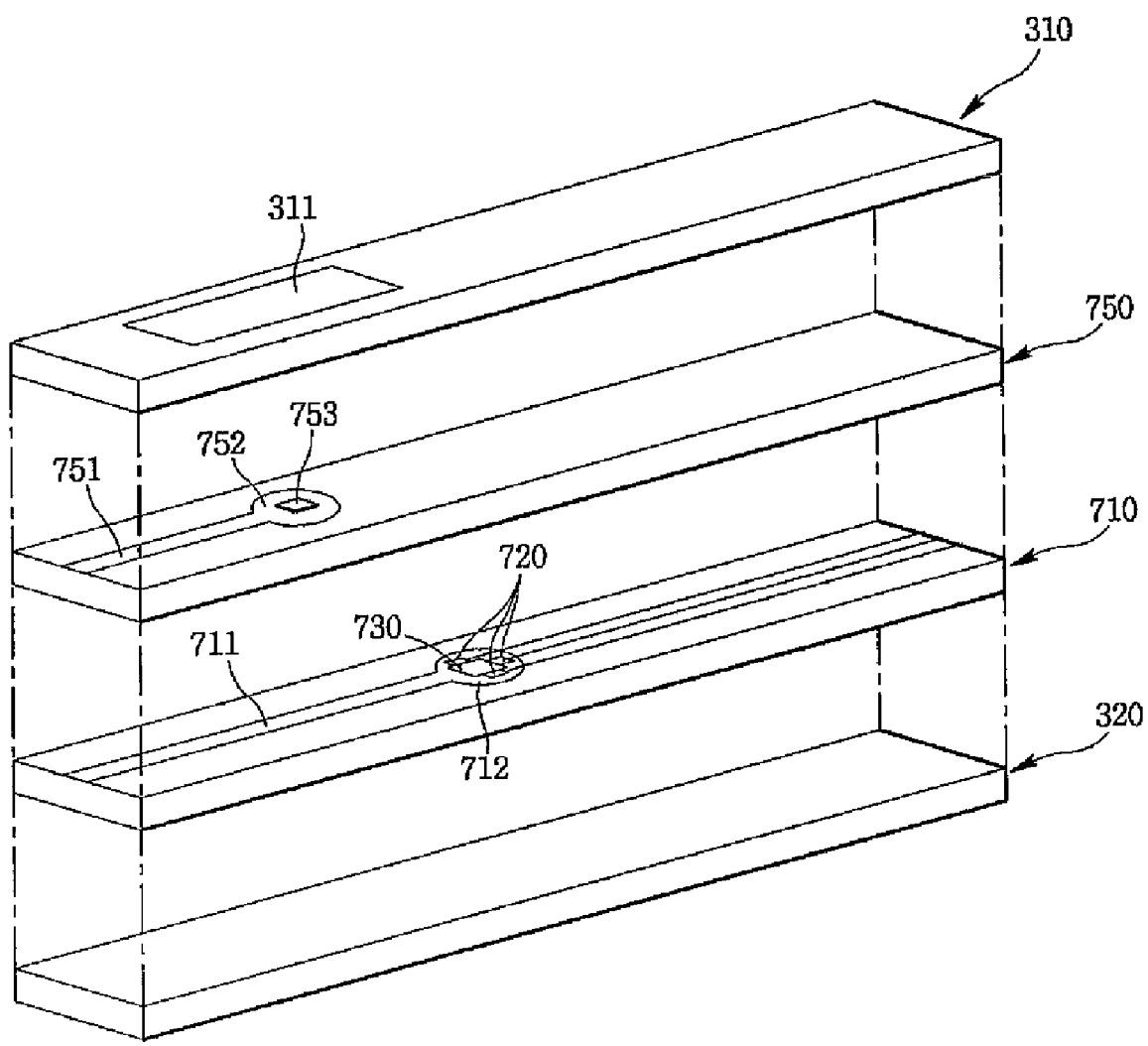
FIG. 8 illustrates an exploded perspective view of a multi-layer strip for measuring a biological material according to another embodiment of the present invention.

FIG. 8 illustrates an exploded perspective view of a multi-layer strip for measuring a biological material according to another embodiment of the present invention. Referring to FIG. 8, the multi-layer strip includes a stack of a plurality of strips 750 and 710. The strip 750 optically measures a biological material, and the strip 710 electrochemically measures a biological material.

Alternatively, the multi-layer strip may include a stack of a plurality of strips and a strip for electrochemically measuring a biological material.

The multi-layer strip may also include upper and lower cover strips 310 and 320. The upper cover strip 310 may include a transparent region 311 which can transmit light therethrough so that the light can reach a reaction unit 752 of the strip 750.

The strips 710 and 750 include flow channels 711 and 751, respectively, through which a biological material can be injected into the multi-layer strip, and reaction units 712 and 752, respectively, which react with the biological material.

A reaction-inducing material layer 753 is immobilized in the reaction unit 752 of the strip 750.

A sensing electrode pattern 720 is formed in the reaction unit 712 of the strip 710, and a reaction-inducing material layer 730 is formed on the sensing electrode pattern 720.

The multi-layer strip of the embodiment of FIG. 8 can measure a biological material optically and electrochemically.

Figure 9:
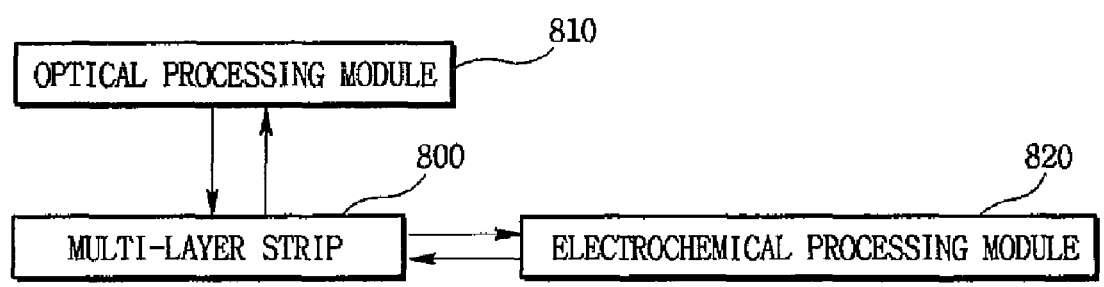
FIG. 9 illustrates a block diagram of a system for measuring a biological material according to an embodiment of the present invention.

FIG. 9 illustrates a block diagram of a system for measuring a biological material according to an embodiment of the present invention. Referring to FIG. 9, the system includes a multi-layer strip 800 and an optical processing module 810 which optically measures the degree of reaction of a biological material with a plurality of reaction-inducing material layers immobilized in the multi-layer strip 800 and quantitatively analyzes the results of the measurement.

The system may also include an electrochemical processing module 820 which electrochemically measures the degree of reaction of a biological material with the reaction-inducing material layers immobilized in the multi-layer strip 800 and quantitatively analyzes the results of the measurement.

Once a biological material is injected into the multi-layer strip 800, the system can measure and quantitatively analyze the biological material by detecting color variations and signal variations resulting from the reaction of the biological material with the reaction-inducing material layers in the multi-layer strip 800 with the aid of the optical processing module 810 and the electrochemical processing module 820.

The optical processing module 810 may include a light emitter which irradiates light onto a reaction point in the multi-layer strip 800; a light receiver which receives light reflected from or transmitted through the reaction point; and an analysis unit which quantitatively analyzes a specific material in a biological material injected into the multi-layer strip 800 based on the amount of light received by the light receiver.

The analysis unit of the optical processing module 810 may include a monitor. In this case, a user may monitor the color of each reaction point in the multi-layer strip 800 through the monitor.

The electrochemical processing module 820 quantitatively analyzes a specific material in a biological material injected into the multi-layer strip 800 by applying a voltage to a sensing electrode pattern of the multi-layer strip 800 and detecting a current variation resulting from the reaction of the biological material with a reaction-inducing material layer on the sensing electrode pattern.

Figure 10:
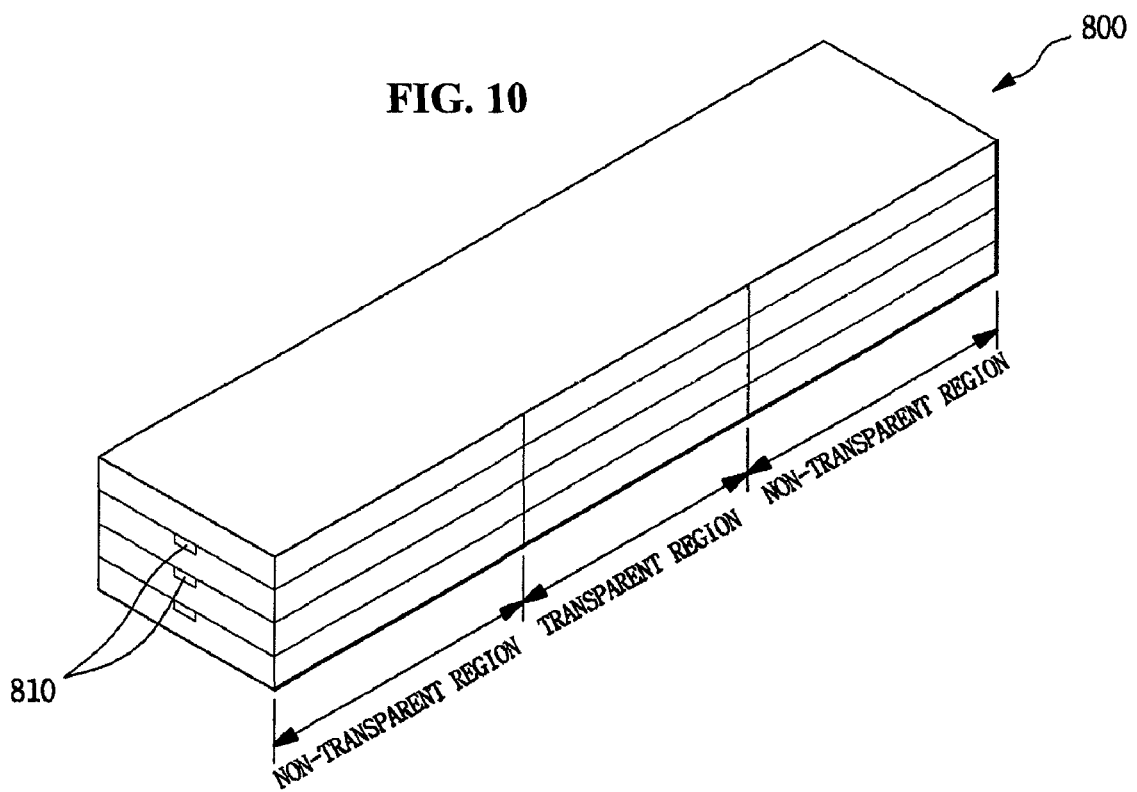
FIG. 10 illustrates a perspective view of a multi-layer strip for measuring a biological material according to another embodiment of the present invention.

FIG. 10 illustrates a perspective view of a multi-layer strip for measuring a biological material according to another embodiment of the present invention. Referring to FIG. 10, a transparent region is formed on a sidewall of a stack 800 of a plurality of strips. The transparent region can transmit light therethrough so that the light can reach the reaction units of the strips.

Since the transparent region is formed on a sidewall of the stack 800, there is no need to form a transparent region in each of the strips. Therefore, it is possible to facilitate the manufacture of a multi-layer strip.

The strips may all be transparent strips, and a portion of a sidewall of the stack 800 not covered with an opaque material layer may be defined as the transparent region.

A distal end formed at each flow channel 810, which are formed in the respective strips, may be exposed on one side of the stack 800.

Figure 11:
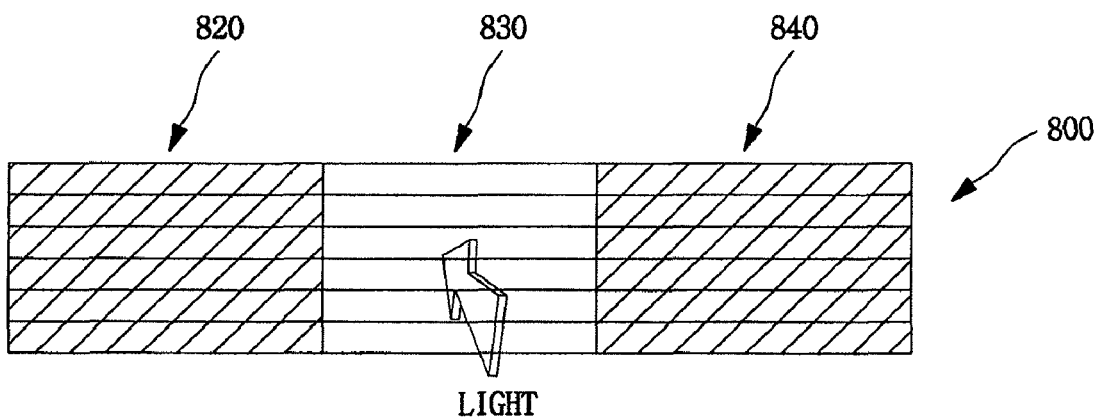
FIG. 11 illustrates a diagram of an embodiment of the multi-layer strip illustrated in FIG. 10, which is partially covered with an opaque material layer.

FIG. 11 illustrates a diagram of a multi-layer strip partially covered with an opaque material layer, according to an embodiment of the present invention. Referring to FIG. 11, in order to form a transparent region on one sidewall of a stack 800 of a plurality of strips as performed in the embodiment of FIG. 10, an opaque material layer may be partially formed on a sidewall of the stack 800.

Then, portions of the sidewall of the stack 800 covered with the opaque material layer are defined as opaque regions 820 and 840, whereas a portion of the sidewall of the stack 800 covered with the opaque material layer is defined as a transparent region 830. As a result, light irradiated for measuring the reaction of a biological material can penetrate into the stack 800 only through the transparent region 830.

As described above, according to the present invention, a multi-layer strip includes a stack of a plurality of strips, each having a flow channel and a reaction unit, and the strips may react with specific materials contained in a biological material injected into the multi-layer strip. Thus, it is possible to quantitatively analyze various materials contained in a biological material. In addition, it is possible to optically and electrochemically measure and quantitatively analyze various materials in a biological material.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A multi-layer strip for use in measuring a biological material, the multi-layer strip comprising:
   a stack of a plurality of strips, each strip comprising a flow channel through which a biological material can be injected into the multi-layer strip and a reaction unit configured to react with the biological material, wherein the reaction units of the strips are configured not to overlap each other so that light perpendicularly incident upon the multi-layer strip can smoothly transmit through the multi-layer strip; and
   a plurality of reaction-inducing material layers respectively immobilized in the reaction units of the strips and configured to react with the biological material.

2. The multi-layer strip of claim 1, wherein the reaction-inducing material layers are configured to react respectively with different specific materials contained in the biological material.

3. The multi-layer strip of claim 1,
   wherein each strip comprises a transparent region configured to transmit light therethrough so that the light can reach the reaction unit of a corresponding underlying strip.

4. The multi-layer strip of claim 1, further comprising:
   upper and lower cover strips which are stacked onto the top and the bottom, respectively, of the stack,
   wherein at least one of the upper and lower cover strips comprises a transparent region configured to transmit light therethrough so that the light can reach the reaction units of the strips.

5. The multi-layer strip of claim 1, wherein the flow channels and the reaction units are formed as grooves or through holes.

6. The multi-layer strip of claim 1, further comprising:
   a plurality of sensing electrode patterns which are respectively formed in the reaction units of the strips,
   wherein each of the reaction-inducing material layers is formed on the respective sensing electrode pattern.

7. The multi-layer strip of claim 1, wherein the biological material is a body fluid.

8. The multi-layer strip of claim 4, wherein at least one of the upper and lower cover strips is a transparent strip partially covered with an opaque material layer, and a region of the at least one strip not covered with the opaque material layer is the transparent region.

9. The multi-layer strip of claim 1, wherein each of the strips is one of the following:
- a strip configured to be exposed to light for optically analyzing at least one aspect of the biological material; or
- an electrochemical strip for electrochemically analyzing at least one aspect of the biological material.

10. The multi-layer strip of claim 1, wherein a distal end formed at each flow channel is exposed on one side of the stack.

11. The multi-layer strip of claim 10, wherein each of the flow channels is formed with a fine width to transmit a liquid-phase biological material to the respective reaction unit through a capillary phenomenon.

12. The multi-layer strip of claim 11, wherein the flow channels are nano channels.

13. The multi-layer strip of claim 1, wherein a transparent region is partially formed on a sidewall of the stack and is configured to transmit light therethrough so that the light can reach the reaction units of the strips.

14. The multi-layer strip of claim 13, wherein the strips are transparent strips partially covered with an opaque material layer, and regions of the strips not covered with the opaque material layer are defined as transparent regions.

15. A multi-layer strip for measuring a biological material, the multi-layer strip comprising:
- a stack of a plurality of strips including at least one electrochemical strip for electrochemically measuring a reaction of a biological material, and at least one strip for optically measuring a reaction of a biological material, each strip comprising a flow channel through which the biological material can be injected into the multi-layer strip and a reaction unit configured to react with the biological material, wherein the reaction units of the strips are configured to not overlap each other so that light perpendicularly incident upon the multi-layer strip can smoothly transmit through the multi-layer strip; and
- a plurality of reaction-inducing material layers respectively disposed in the reaction units of the strips and configured to react with specific materials contained in the biological material.

16. The multi-layer strip of claim 15, wherein the electrochemical strip comprises a sensing electrode pattern formed in the respective reaction unit, and the respective reaction-inducing material layer is formed on the sensing electrode pattern.

17. The multi-layer strip of claim 15, wherein a distal end formed at each flow channel is exposed at one side of the stack.

18. A system for measuring a biological material, the system comprising:
- a multi-layer strip which includes a stack of a plurality of strips and a plurality of reaction-inducing material layers, each strip comprising a flow channel through which at least one biological material can be injected into the multi-layer strip and a reaction unit configured to react with the biological material, the reaction-inducing material layers being immobilized in the reaction units of the strips and configured to react with the biological material, wherein the reaction units of the strips are configured to not overlap each other so that light perpendicularly incident upon the multi-layer strip can smoothly transmit through the multi-layer strip; and
- at least one of an optical processing module and an electrochemical processing module, for optically and/or electrochemically analyzing the multi-layer strip.

19. The system of claim 18, wherein the optical processing module is configured to optically measure a degree of reaction of the biological material with the reaction-inducing material layers and to quantitatively analyze results of the optical measurement.

20. The system of claim 18, wherein at least one of the strips comprises a sensing electrode pattern formed in the respective reaction unit, and the electrochemical processing module is configured to electrochemically measure a degree of reaction of the biological material with the reaction-inducing material layers and to quantitatively analyze results of the electrochemical measurement.

* * * * *